United States Patent [19]

Hergenrother et al.

[11] Patent Number: 5,496,294
[45] Date of Patent: Mar. 5, 1996

[54] CATHETER WITH KINK-RESISTANT DISTAL TIP

[75] Inventors: Robert Hergenrother, Fremont; June Lim, Union City; Roger Farnholtz, Fremont; Kim Nguyen, Milpitas; Edward Snyder, San Jose, all of Calif.

[73] Assignee: Target Therapeutics, Inc., Fremont, Calif.

[21] Appl. No.: 273,049

[22] Filed: Jul. 8, 1994

[51] Int. Cl.⁶ .................................................. A61M 25/00
[52] U.S. Cl. ............................................ 604/282; 604/264
[58] Field of Search ............................. 604/282, 281, 604/280, 53, 43, 44, 45, 264

[56] References Cited

U.S. PATENT DOCUMENTS

| | | |
|---|---|---|
| 2,437,542 | 3/1948 | Krippendorf . |
| 3,174,851 | 3/1965 | Buehler et al. . |
| 3,351,463 | 11/1967 | Rozner et al. . |
| 3,416,531 | 12/1968 | Edwards . |
| 3,568,660 | 3/1971 | Crites et al. . |
| 3,753,700 | 8/1973 | Harrison et al. . |
| 3,890,976 | 6/1975 | Bazell et al. . |
| 3,924,632 | 12/1975 | Cook . |
| 4,425,919 | 1/1984 | Alston, Jr. et al. . |
| 4,484,586 | 11/1984 | McMickle et al. . |
| 4,516,972 | 5/1985 | Samson . |
| 4,571,240 | 2/1986 | Samson et al. . |
| 4,610,674 | 9/1986 | Suzuki et al. . |
| 4,636,346 | 1/1987 | Gold et al. . |
| 4,705,511 | 11/1987 | Kocak . |
| 4,739,768 | 4/1988 | Engelson . |
| 4,775,371 | 10/1988 | Mueller, Jr. et al. . |
| 4,806,182 | 2/1989 | Rydell et al. . |
| 4,832,681 | 5/1989 | Lenck . |
| 4,840,622 | 6/1989 | Hardy . |
| 4,863,442 | 9/1989 | DeMello et al. . |
| 4,886,506 | 12/1989 | Lovgren et al. . |
| 4,898,591 | 2/1990 | Jang et al. . |
| 4,994,069 | 2/1991 | Ritchart et al. . |
| 5,037,404 | 8/1991 | Gold et al. . |
| 5,069,674 | 12/1991 | Fearnot et al. . |
| 5,078,702 | 1/1992 | Pomeranz . |
| 5,122,136 | 6/1992 | Guglielmi et al. . |
| 5,176,660 | 1/1993 | Truckai . |
| 5,178,158 | 1/1993 | de Toledo . |
| 5,217,482 | 6/1993 | Keith . |
| 5,221,270 | 6/1993 | Parker . |
| 5,226,911 | 7/1993 | Chee et al. . |
| 5,234,416 | 8/1993 | Macaulay et al. . |
| 5,250,071 | 10/1993 | Palmero . |
| 5,254,107 | 10/1993 | Soltesz . |
| 5,261,916 | 11/1993 | Engelson . |
| 5,279,596 | 1/1994 | Castenada . |
| 5,304,194 | 4/1994 | Chee et al. . |
| 5,304,195 | 4/1994 | Twyford, Jr. et al. . |
| 5,306,252 | 4/1994 | Yutori et al. ......................... 604/164 |
| 5,312,415 | 5/1994 | Palmero . |
| 5,334,171 | 8/1994 | Kaldany ................................ 604/282 |
| 5,342,295 | 8/1994 | Imran .................................... 604/43 |

*Primary Examiner*—John D. Yasko
*Attorney, Agent, or Firm*—Morrison & Foerster

[57] ABSTRACT

This invention is a surgical device. In particular, it is a catheter suitable for treating a tissue target within the body, which target is accessible through the vascular system. Central to the invention is the use of a multi-component distal section having an interior stiffener and an exterior tubing member.

16 Claims, 2 Drawing Sheets

CATHETER WITH KINK-RESISTANT DISTAL TIP

FIELD OF THE INVENTION

This invention is a surgical device. In particular, it is a catheter suitable for treating a tissue target within the body, which target is accessible through the vascular system. Central to the invention is the use of a multi-component distal section having an interior stiffener and an exterior tubing member.

BACKGROUND OF THE INVENTION

Catheters are increasingly used to access remote regions of the human body and, in doing so, delivering diagnostic or therapeutic agents to those sites. In particular, catheters which use the circulatory system as the pathway to these treatment sites are especially useful. For instance, it is commonplace to treat diseases of the circulatory system via angioplasty (PCTA) using catheters having balloons on their distal tips. It is similarly common that those catheters are used to deliver a radiopaque agent to that site prior to the PCTA procedure to allow viewing of the problem prior to treatment.

Often the target which one desires to access by catheter is within a soft tissue such as the liver or the brain. The difficulty in reaching such a site must be apparent even to the casual observer. The catheter must be introduced through a large artery such as those found in the groin or the neck and be passed through ever narrower regions of the arterial system until the catheter reaches a selected site. Often such pathways will wind back upon themselves in a multi-looped path. These catheters are difficult to design and use in that they must be fairly stiff at their proximal end so to allow the pushing and manipulation of the catheter as it progresses through the body, and yet must be sufficiently flexible at the distal end to allow passage of the catheter tip through the loops and increasingly smaller blood vessels mentioned above. Yet, at the same time, the catheter must not cause significant trauma to the blood vessel or to the surrounding tissue. Further details on the problems and an early, but yet effective, way of designing a catheter for such a traversal may be found in U.S. Pat. No. 4,739,768, to Engelson. The Engelson catheters are designed to be used with a guidewire. A guidewire is simply a wire, typically of very sophisticated design, which is the "scout" for the catheter. The catheter fits over and slides along the guidewire as it passes through the vasculature. Said another way, the guidewire is used to select the proper path through the vasculature with the urging of the attending physician and the catheter slides along the guidewire once the proper path is established.

There are other ways of causing a catheter to proceed through the human vasculature to a selected site, but a guidewire-aided catheter is considered to be both quite quick and somewhat more accurate than the other procedures.

Once the guidewire and the catheter reach the chosen target, the guidewire is typically then removed so to allow treatment or diagnostic procedures to begin. The invention here is especially suitable for placement of vasoocclusive devices. These treatment devices have been known to hang within the lumens of catheters not having special provisions to assure that those inner lumen are generally obstruction-free.

Typical of the vasooclusive devices suitable for use with this catheter are those found in U.S. Pat. No. 4,994,069, to Ritchart et al, (vasoocclusive coils); U.S. Pat. No. 5,122,136, to Guglielmi et al (electrolytically detachable vasooclusive coils); U.S. Pat. Nos. 5,226,911 and 5,304,194, to Chee et al (vasooclusive coils with attached fibers); U.S. Pat. No. 5,250,071, to Palermo (mechanically detachable coils); U.S. Pat. No. 5,261,916, to Engelson (mechanically detachable coil); U.S. Pat. No. 5,304,195, to Twyford et al (mechanically detachable coils); and U.S. Pat. No. 5,312,415, to Palermo (mechanically detachable coils); the entirety of which are incorporated by notice. These devices each have a relatively rigid diameter and must be pushed through the lumen of the delivery catheter. Modest kinks in the smaller diameter lumens found in the distal regions of the catheter may cause major problems with delivery. The creation of relatively kink-free interior regions is the goal of this invention. We have found that use of fine ribbons of superelastic alloys wound helically about the interior of the catheter distal region and carefully chosen combinations of thin polymeric tubing in that distal region each garner excellent kink resistance without raising the distal section stiffness to an unacceptable level.

The use of ribbons in winding a catheter body is not a novel concept. However, none have used this concept to produce a catheter which has the physical capabilities of the catheter of this invention.

Examples of previously disclosed catheters include U.S. Pat. No. 2,437,542, to Crippendorf. Crippendorf describes a "catheter-type instrument" which is typically used as a ureteral or urethral catheter. The physical design is said to be one having a distal section of greater flexibility and a proximal section of lesser flexibility. The device is made of intertwined threads of silk, cotton, or some synthetic fiber. It is made by impregnating a fabric-based tube with a stiffening medium which renders the tube stiff yet flexible. The thus-plasticized tubing is then dipped in some other medium to allow the formation of a flexible varnish of material such as a tung oil base or a phenolic resin and a suitable plasticizer. There is no indication that this device is of the flexibility required herein. Additionally, it appears to be the type which is used in some region other than in the periphery or in soft tissues of the body.

Similarly, U.S. Pat. No. 3,416,531, to Edwards, shows a catheter having braiding-edge walls. The device further has layers of other polymers such as TEFLON and the like. The strands found in the braiding in the walls appear to be threads having classic circular cross-sections. There is no suggestion of constructing a device using ribbon materials. Furthermore, the device is shown to be fairly stiff in that it is designed so that it may be bent using a fairly large handle at its proximal end. There is no suggestion to either merely wind ribbon onto a polymeric substrate to form a catheter or, in particular, to make one of such flexibility as is required herein.

U.S. Pat. No. 4,484,586 shows a method for the production of a hollow, conductive medical tubing. The conductive wires are placed in the walls of hollow tubing specifically for implantation in the human body, particularly for pacemaker leads. The tubing is made of, preferably, an annealed copper wire which has been coated with a body-compatible polymer such as a polyurethane or a silicone. The copper wire is coated and then used in a device which winds the wire into a tube. The wound substrate is then coated with another polymer to produce a tubing having spiral conducting wires in its wall.

A document showing the use of a helically wound ribbon of flexible material in a catheter is U.S. Pat. No. 4,516,972, to Samson. This device is a guiding catheter and it may be produced from one or more wound ribbons. The preferred ribbon is an aramid material known as Kevlar 49. Again, this device is a device which must be fairly stiff. It is a device which is designed to take a "set" and remain in a particular configuration as another catheter is passed through it. It must be soft enough so as not to cause substantial trauma, but it is certainly not for use as a guidewire. It would not meet the flexibility criteria required of the inventive catheter described herein.

U.S. Pat. No. 4,705,511, to Kocak, shows an introducer sheath assembly having a having a helically spaced coil or braid placed within the wall of the device. The disclosed device is shown to be quite stiff, in that it is intended to support other catheters during their introduction in to the human body.

U.S. Pat. No. 4,806,182, to Rydell et al., shows a device using stainless steel braid imbedded in its wall and an inner layer of a polyfluorocarbon. The process also described therein is a way to laminate the polyfluorocarbon onto a polyurethane inner liner so as prevent delamination.

U.S. Pat. No. 4,832,681, to Lenck, shows a method and apparatus for artificial fertilization. The device itself is a long portion of tubing which, depending upon its specific materials of construction, may be made somewhat stiffer by the addition of spiral reinforcement comprising stainless steel wire.

Another catheter showing the use of braided wire is shown in U.S. Pat. No. 5,037,404, to Gold et al. Mention is made in Gold et al of the concept of varying the pitch angle between wound strands so to result in a device having differing flexibilities at differing portions of the device. The differing flexibilities are caused by the difference in pitch angle. No mention is made of the use of ribbon, nor is any specific mention made of the particular uses to which the Gold et al. device may be placed.

U.S. Pat. No. 5,069,674 shows a small diameter epidural catheter which is flexible and kink-resistant when flexed. The wall has a composite structure including a helical coil, typically stainless steel or the like, a tubular sheath typically of a polymer, and a safety wire which is spiraled about the coil and is often in the shape of a ribbon.

U.S. Pat. No. 5,176,660 shows the production of catheters having reinforcing strands in their sheath wall. The metallic strands are wound throughout the tubular sheath in a helical crossing pattern so to produce a substantially stronger sheath. The reinforcing filaments are used to increase the longitudinal stiffness of the catheter for good "pushability". The device appears to be quite strong and is wound at a tension of about 250,000 lb./in.$^2$ or more. The flat strands themselves are said to have a width of between 0.006 and 0.020 inches and a thickness of 0.0015 and 0.004 inches. There is no suggestion to use these concepts in devices having the flexibility and other configurations described below.

U.S. Pat. No. 5,178,158, to de Toledo, shows a device which is a convertible wire having use either as a guidewire or as a catheter. The coil appears to be a ribbon which forms an internal passage through the coil/catheter device. No interior coating is applied.

U.S. Pat. No. 5,217,482 shows a balloon catheter having a stainless steel hypotube catheter shaft and a distal balloon. Certain sections of the device shown in the patent use a spiral ribbon of stainless steel secured to the outer sleeve by a suitable adhesive to act as a transition section from a section of very high stiffness to a section of comparatively low stiffness.

U.S. Pat. No. 5,279,596, to Castaneda et al, suggests the use of an embedded coil in the distal region of an angioplasty or angiography catheter to improve its kink-resistance. However the patent discloses neither the use of high-elasticity alloys in the coil nor does it suggest the use of the resulting catheters as the vehicles for vasoocclusive device delivery.

Similarly, multi-layer catheter distal sections are not, in and of themselves, unique.

U.S. Pat. No. 4,636,346, to Gold et al., shows a thin wall guiding catheter having a distal end which is adapted to be formed into a curved configuration and passed through various branching blood vessels or the like. It has a lubricious inner sheath, a rigid intermediate sheath, and a flexible outer sheath. The distal tip itself is of similar construction but the rigid intermediate sheath is sometimes omitted. Since the catheter described there is clearly an introducer catheter—a catheter used because of its rigidity—it is not of the type described herein.

U.S. Pat. No. 4,840,622, to Hardy, shows a cannula which, again, is a multi-layer device used to direct another catheter from the exterior of a human body to some, typically, known position within the human body.

U.S. Pat. No. 4,863,442, to DeMello et al., shows a guide catheter having a tubular body with a wire-braided TEFLON core in a polyurethane jacket. The distal end of the jacket is removed form the core and a soft polyurethane tip is applied to the core over the region where the jacket has been removed. This results in a generally soft tipped but fairly stiff catheter mode up of multiple layers.

U.S. Pat. No. 5,078,702, to Pomeranz, shows a soft tip catheter, typically a guide catheter, having multiple sections of varying materials and inner and outer sheaths making up the catheter shaft. However, the intent of Pomeranz is not to produce a catheter having kink resistance, it is instead to form a soft catheter having significant stiffness. It should be noted that the material used in the inner sheath is said to be of a fairly rigid polymer (see column 4).

None of these devices are catheters which have the kink-resistance described below.

SUMMARY OF THE INVENTION

This invention is a distal catheter section made up, desirably, of an outer tubing liner and an inner stiffener placed coaxially within that liner. The inner stiffener may be a spirally wound ribbon of a super-elastic alloy or a polymeric tubing layer. In addition, the outer tubing is desirably of a highly flexible material; particularly desirable is a blend of ethylene vinyl acetate (EVA) and low density polyethylene (LDPE) or linear low density polyethylene (LLDPE). Tubing constructed of this tubing is highly flexible and yet has sufficient wall strength to withstand catheter pressurization without substantial radial strain. The interior of the catheter may be further coated or lined with a thin layer of a lubricious polymer such as a polytetrafluoroethylene or other polyfluorocarbon.

The distal catheter section may be included into an integral catheter assembly. Wise choices of materials permit the catheter to be of a smaller overall diameter with a superior critical diameter.

DESCRIPTION OF THE INVENTION

This invention is a kink-resistant catheter distal section and catheter incorporating that section. It is a composite section including an outer covering with an inner stiffener. The inner stiffener may be a helically wound ribbon stiffener coaxially incorporated into that section or sections. The inner stiffener may instead be a high flexibility urethane or polyethylene. Desirably, the catheter section has a critical bend diameter of no more than about 6.0 mm, preferably no more than 4.5 mm. Additionally, that section desirably has a lateral stiffness, measured as an axil deflection force of no more than about 3.0 gm, preferably no more than about 2.2 gm.

Figure 1:
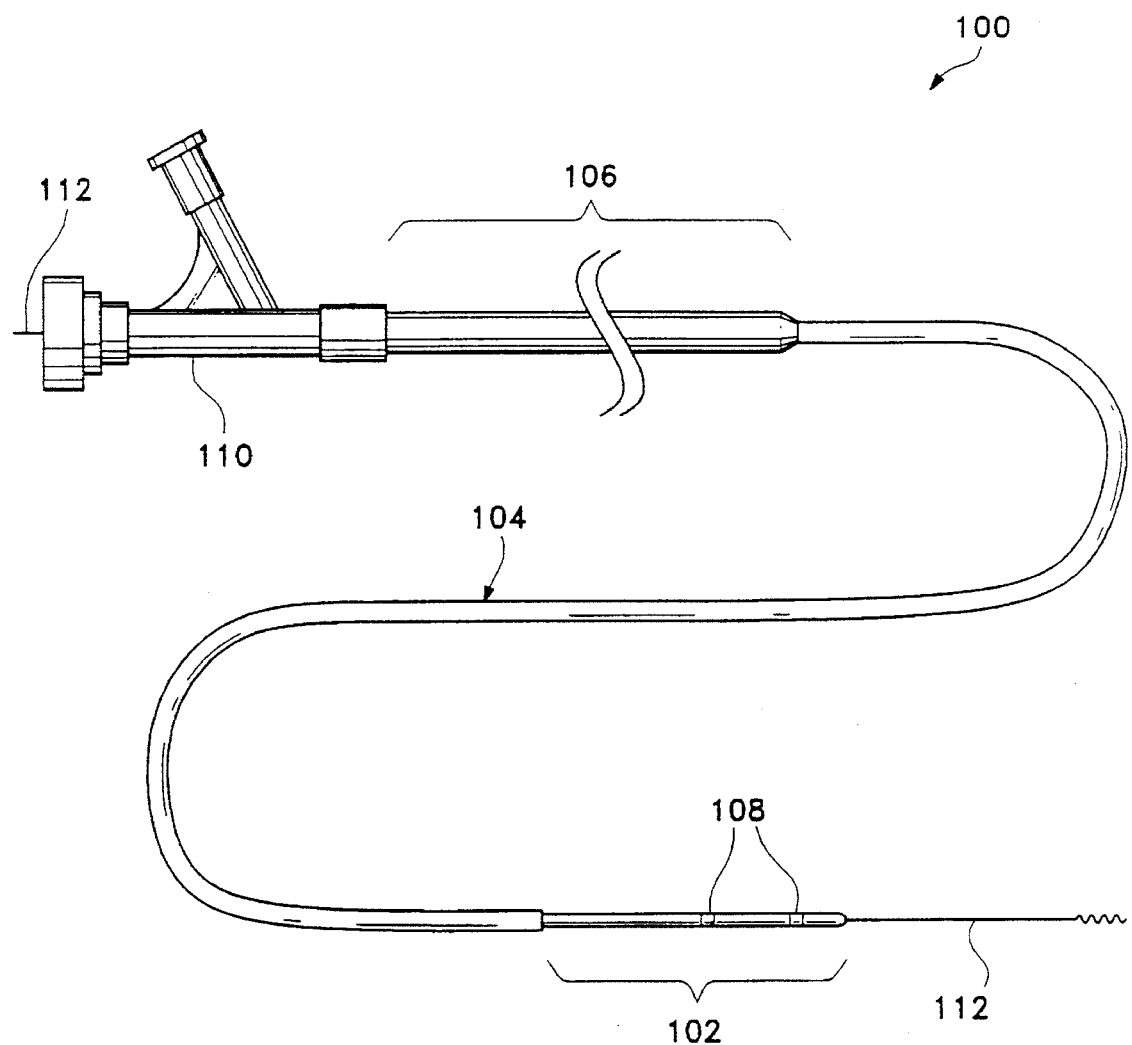
FIG. 1 shows, in side view, a typical three section catheter which may incorporate the distal section of the invention.

A typical multi-section catheter (100) which may incorporate the concepts of this invention is shown in FIG. 1. Such a catheter is described in more detail in U.S. Pat. No. 4,739,768, to Engelson, (the entirety of which is incorporated by reference) and is suitable for neurological and peripheral vascular applications. Clearly, then, it is also suitable for less demanding service such as might be encountered in access and treatment of the heart. One difficulty which has arisen as higher demands for length have been placed on these catheters is that the diameter of the distal section necessarily becomes smaller and smaller. This is so since the longer catheters must reach ever more distal and, hence, smaller vascular areas. This smaller diameter requires a concomitant thinning of the wall section. The thinner section walls may kink or ripple when actively pushed along the guidewire or when placed in a curved vessel or when the noted vasoocclusive devices are pushed through the catheter's lumen. The typical configuration shown in FIG. 1 has a distal section (102) having significant flexibility, an intermediate section (104) which is typically less flexible, and a long proximal section (106) which in turn is least flexible. The distal section (102) is flexible and soft to allow deep penetration into the extraordinary convolutions of the neurological vasculature without trauma. Various known and necessary accessories to the catheter assembly, e.g., one or more radiopaque bands (108) at the distal region to allow viewing of the position of the distal region under fluoroscopy and a luer assembly (110) for guidewire (112) and fluids access, are also shown in FIG. 1. The typical dimensions of this catheter are:

| Overall length: | 60–200 cm |
| Proximal Section (106): | 60–150 cm |
| Intermediate Section (104): | 20–50 cm |
| Distal Section (102): | 2.5–30 cm |

Obviously, these dimensions are not particularly critical to this invention and are selected as a function of the malady treated and its site within the body.

Figure 2:
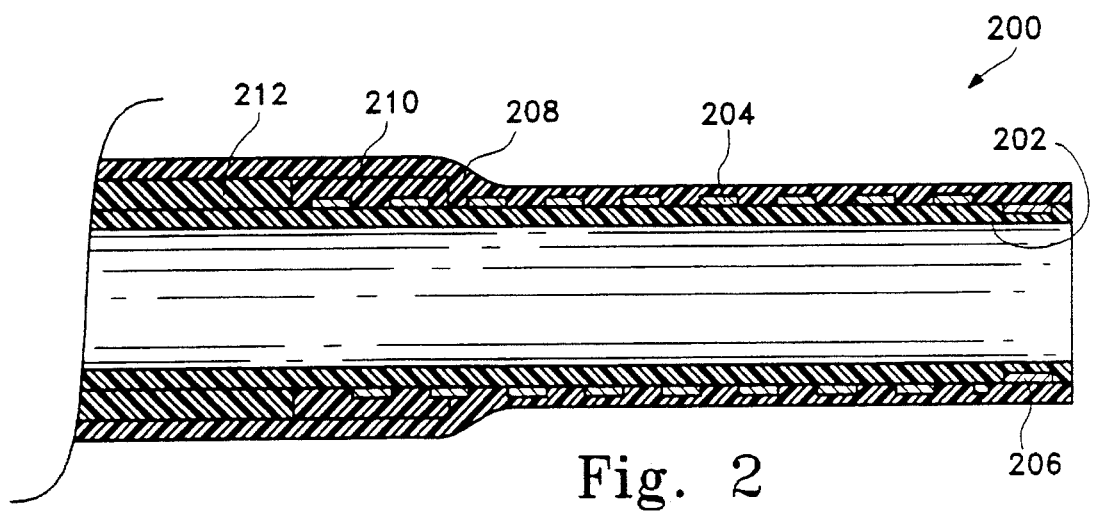
FIGS. 2, 3, and 4 show, in magnification, fragmentary cross-sections of catheter sections made according to this invention.

FIG. 2 shows a magnified section of a catheter body or section (200) showing the most basic aspects of one variation of the invention. As shown there, the catheter body or section has an optional inner tubing member (202) and a helically wound ribbon (204). The optional inner tubing member (202) may be of any of a variety of lubricious polymers, e.g., polytetrafluoroethylene, FEP, or other fluorocarbon polymers or polysulfones. The optional inner liner (202) should not be any thicker than about 0.0005" in wall thickness so to preserve the flexibility of the distal section (200).

It should also be noted that each of the polymers discussed herein may be used in conjunction with radiopaque material such as barium sulfate, bismuth trioxide, bismuth carbonate, powdered tungsten, powdered tantalum, or the like so that the location of the various pieces of tubing may be radiographically visualized within the vessel. A tradeoff in decreased flexibility is typically encountered when radio-opacifiers are added to the polymeric mix, however.

The spiral wound ribbon (204) shown in FIG. 2 may also be of a variety of different materials. The class of alloys known as super-elastic alloys is most desirable even though the processability of these alloys into small ribbons is not routine. Preferred super-elastic alloys include the class of materials known as nitinol—alloys discovered by the U.S. Navy Ordnance Laboratory. See, for instance, U.S. Pat. Nos. 3,174,851 to Buehler et al., 3,351,463 to Rozner et al., and 3,753,700 to Harrison et al. However, the '700 patent describes a less desirable material because of its higher modulus due to an increased iron content. These metals are characterized by their ability to be transformed from an austenitic crystal structure to a stress-induced-martensitic (SIM) structure at certain temperatures, and return elastically to the austenitic structure when the stress is removed. These alternating crystalline structures provide the alloy with its super-elastic properties. One such well-known alloy, nitinol, is a nickel-titanium alloy. It is readily commercially available and undergoes the austenite-SIM-austenite transformation at a variety of temperature ranges.

These alloys are especially suitable because of their capacity to elastically recover almost completely to the initial configuration once the stress is removed. Typically there is little plastic deformation, even at relatively high strains. This feature allows the stiffener to be exceptionally small, undertake substantial bends as the vasoocclusive device passes through it, and yet return to its original shape once the stress has been relieved.

Metallic ribbons (204) that are suitable for use in this invention are desirably between 0.5 mil and 1.0 mil in thickness and 2.5 mil and 8.0 mil in width. Preferred, based on strength, cost and availability are ribbons of 0.5 mil.×2 mil., 2 mil.×6 mil., and 2 mil.×8 mil. Especially preferred is a ribbon of 0.5 mil.×2 mil.

Also shown in FIG. 2 is a radiopaque marker (206) of platinum or other suitably dense material so to allow the physician using the catheter to radiographically visualize the position of the distal tip of the catheter.

The outer tubing (208) of the catheter section (200) is typically a shrink-wrap polyethylene often blended with an EVA copolymer up to about 10% by weight and having a wall thickness of between 0.5 mils and 2.0 mils. These polymers are then cross-linked by radiation to increase its strength. Polyurethanes and polyvinylchlorides having a similar softness (Durometer reading) and flexibility are also suitable. However, as will be explained below, we have found that substitution of a polymer having even softer, more flexible characteristics while maintaining the overall wall strength is desirable.

Returning to FIG. 2, the stiffener ribbon (204) may be simply wound onto the optional inner tubing liner (202) when such a lining is used. The stiffener ribbon (204) may be applied with an adhesive. The adhesive is used primarily to cause the outer cover to adhere to the inner tubing liner (202). When the inner liner (202) is not used, the stiffener ribbon (204) may be pre-wound and the outer tubing shrinkwrapped onto the coil. Spacer (210) is used to hold the various components in place during assembly and typically is of a polyethylene material which is melt compatible with the outer liner (208). Section (212) is the inner liner on the midsection of the catheter assembly.

Figure 3:
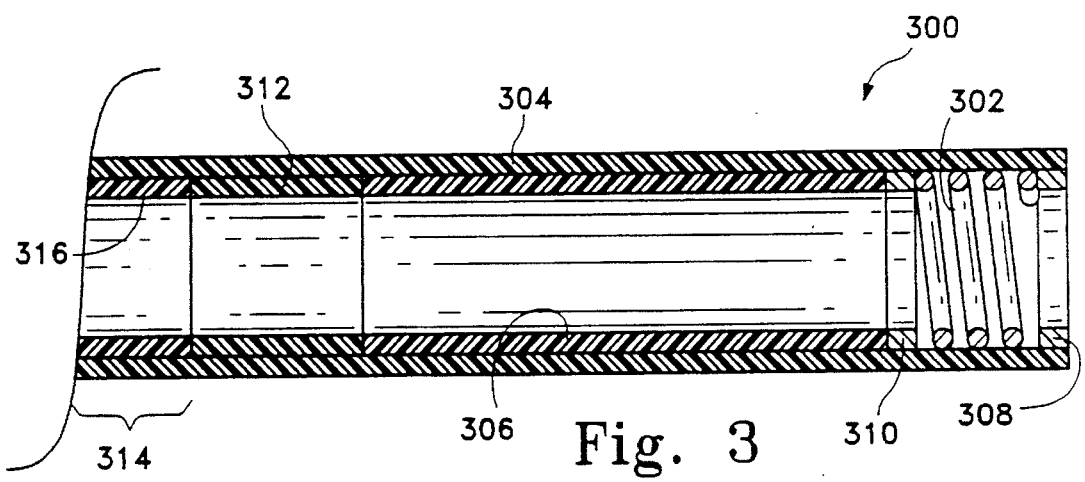
Figure 4:
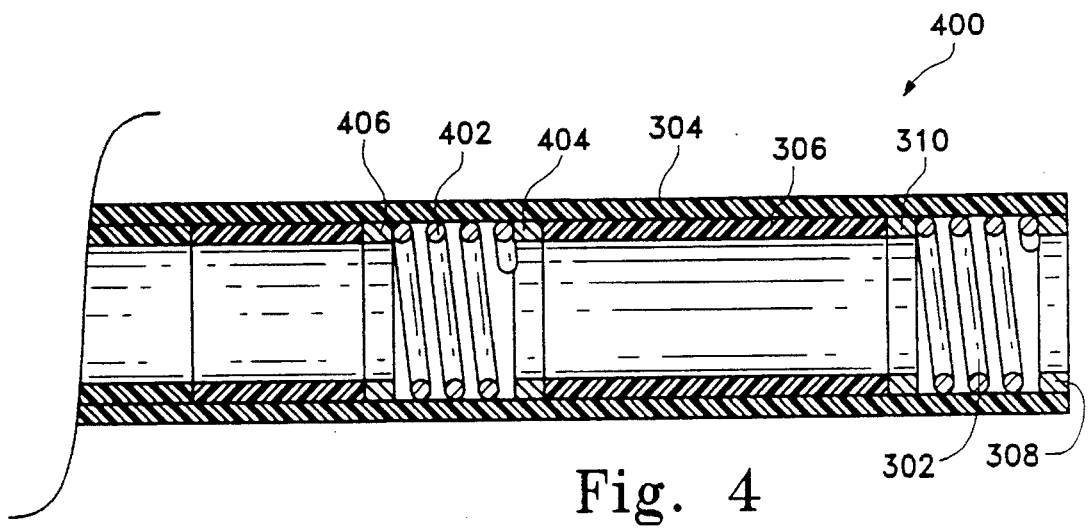

FIGS. 3 and 4 show two related variations of the inventive distal section involving either a single radiopaque marker (FIG. 3) or double radiopaque markers (FIG. 4). The presence of the comparatively inflexible radiopaque markers in the extremely flexible distal section of these catheters represents exceptional challenges in producing a kink-resistant tube. The challenge is especially acute when the two-marker variation is considered. Under high flexure, the region just adjacent the markers is likely to kink and then bind upon advancement of the relatively rigid vasoocclusive devices, particularly when the diameter of the vasooclusive device is close in size to the inner diameter of the open lumen. We have found that the use of a single layer of a polymer (often a polyethylene shrinkable tubing) which is flexible enough to function effectively as a distal section for tracking through the cerebral vasculature often is insufficiently strong to maintain its interior shape in the critical region near the radiopaque markers. Increasing the thickness of the layer to alleviate the kinking problem raises the stiffness of the section often to marginally unacceptable levels. By combining two layers of closely matched tubing materials in an overall thickness typically no greater than the thickness of the marker, the dual goals of enhanced kink-resistance and acceptable flexibility may be met especially when the abuts the marker rather than over- or under-lapping the marker.

FIG. 3 shows a distal section (300)having a single distal radiopaque marker (302). In this instance, the single radiopaque marker (302) is shown to be a coil although the marker may be a band as is shown in FIG. 2. In this variation, the combination of the outer tubing (304) and the thinner may be strengthened in this region of the catheter by the introduction of the thin inner stiffener layer (306). Also shown are a variety of spacer sections used to hold various components in place during assembly and to maintain those position during later use. These sections are the distal radiopaque coil marker spacers (308 and 310) and the transition spacer (312) between the distal section of the catheter and the midsection (314). The inner liner (316) in that midsection (314) is also shown. In some instances, it may not be necessary to utilize an independent midsection but instead a single proximal section may abut the transition spacer (312).

Although the outer layer (304) may be of a wide variety of materials such as polyurethanes, polyvinyl chloride, LDPE, LLDPE, the outer layer (304) is desirably a shrinkable tubing having an EVA content of at least 10% EVA, preferably 12–20% and a wall thickness of 0.0005 to 0.010", preferably about 0.003". The inner liner (306) preferably is a similar composition but with a lower (or, preferably, no) EVA. Specifically, the preferred material is LLDPE or LDPE. The wall thickness of such tubing may be 0.0005 to 0.0020", preferably about 0.0015". The stiffness of this combination of materials typically produces a lateral stiffness measured as an axial deflection force of no more than about 3.0 gm, preferably no more than about 2.2 gm. This stiffness is measured by placing a 3 cm. length of the section in a position normal or directly perpendicular to a plate connected to a meter capable of measuring force against the plate. The section is moved directly perpendicular to the measuring plate and the force measured. The measured force typically increases to a plateau as the section bends against the measuring plate. The value of that measured plateau is value used in assessing the stiffness of the catheter section.

Additionally, this catheter section exhibits high performance kink resistance, e.g., the catheter section has a critical bend diameter of no more than about 6.0 mm, preferably no more about 4 m. This is measured simply by turning a portion of the catheter section into a loop generally as flat as is possible and decreasing the size of the loop until a kink is observed, The diameter at which the kink is observed is the "critical bend diameter."

FIG. 4 shows a distal section (400) similar to that in FIG. 3 with the exception of the presence of an added radiopaque marker (402) located proximally of the inner liner (306). The proximal radiopaque marker (402) also may have added positioning spacers (404 and 406). Distal sections of this design are especially useful in catheters used in conjunction with the Guglielmi vasooclusive devices mentioned above.

It should be apparent that the outer layer (208 in FIG. 2 or 304 in FIGS. 3 and 4) may also be applied by dipping the inner tubing layer (306)/stiffener ribbon (204) into a molten polymer bath or into a polymer dissolved in a solid or into a suspension or latex comprising the outer cover polymer. Obviously, the cover may be placed on the catheter by spraying or otherwise applying the material. Included in such a class are the polyurethanes, polysilicones, polyvinylpyrrolidone, etc.

The catheter and catheter sections of this invention may be coated or otherwise treated both inside and outside to increase their lubricity.

This invention has been described and specific examples of the invention have portrayed. The use of those specifics is not intended to limit the invention in any way. Additionally, to the extent that there are variations of the invention which are within the spirit of the disclosure and yet are equivalent to the inventions found in the claims, it is our intent that this patent cover those variations as well.

We claim as our invention:

1. A catheter section comprising:

an elongate tubular member having a proximal end and a distal end and a passageway defining an inner lumen extending between those ends, the distal end of the elongate tubular member comprising:

a.) an inner stiffener liner of a first liner material in coaxial relationship with an outer tubular cover, b.) an outer tubular cover comprising a polyethylene blend containing at least 12% EVA, and c.) at least a distal radiopaque marker located distally of said inner stiffener liner.

2. The catheter section of claim 1 wherein the inner liner material comprises polyethylene.

3. The catheter section of claim 1 wherein the section has a lateral flexibility measured as a deflection force of no more than 3.0 gm.

4. The catheter section of claim 3 wherein the section has a lateral flexibility measured as a deflection force of no more than 2.2 gm.

5. The catheter section of claim 1 where the liner material and cover material are radiation sterilizable without substantial degradation of their physical attributes.

6. The catheter section of claim 1 where at least one of the liner and cover materials are radiopaque.

7. A catheter section comprising:

an elongate tubular member having a proximal end and a distal end and a passageway defining an inner lumen extending between those ends, the distal end of the elongate tubular member comprising:

a.) an inner stiffener liner of a first liner material comprising a helically wound metallic ribbon stiffener in coaxial relationship with an outer tubular cover, b.) an outer tubular cover comprising a cover material, and c.) at least a distal radiopaque marker located distally of said inner stiffener liner.

8. The catheter section of claim 7 wherein the inner stiffener liner comprises a superelastic alloy.

9. The catheter section of claim 8 wherein the superelastic alloy is nitinol.

10. The catheter section of claim 9 wherein the outer cover material comprises a polyethylene blend containing at least 12% EVA.

11. The catheter section of claim 7 wherein the section has a lateral flexibility measured as a deflection force of no more than 3.0 gm.

12. The catheter section of claim 11 wherein the section has a lateral flexibility measured as a deflection force of no more than 2.2 gm.

13. The catheter section of claim 8 where the ribbon stiffener comprises a ribbon having a thickness between 0.5 mil and 1.0 mil and a width between 2.5 and 8.0 mil.

14. The catheter section of claim 7 wherein the section has a lateral flexibility measured as a deflection force of no more than 3.0 gm.

15. The catheter section of claim 14 wherein the section has a lateral flexibility measured as a deflection force of no more than 2.2 gm.

16. The catheter section of claim 14 where at least one of the liner and cover materials are radiopaque.

\* \* \* \* \*

UNITED STATES PATENT AND TRADEMARK OFFICE

CERTIFICATE OF CORRECTION

PATENT NO. : 5,496,294

DATED : March 5, 1996

INVENTOR(S) : HERGENROTHER et al.

It is certified that error appears in the above-identified patent and that said Letters Patent is hereby corrected as shown below:

column 7, line 28: insert --inner liner-- prior to "abuts".

column 7, line 38: change "position" to --positions--.

column 8, line 7: delete ", The" and insert --. The-- .

column 8, line 31: insert --been-- prior to "portrayed".

*Claim 14, column 10*: cancel in its entirety.

*Claim 15, column 10*: cancel in its entirety.

UNITED STATES PATENT AND TRADEMARK OFFICE
CERTIFICATE OF CORRECTION

PATENT NO. : 5,496,294

DATED : March 5, 1996

INVENTOR(S) : HERGENROTHER et al.

It is certified that error appears in the above-indentified patent and that said Letters Patent is hereby corrected as shown below:

*Claim 16, column 10*: change "claim 14" to --claim 11".

Signed and Sealed this

Seventeenth Day of June, 1997

Attest:

BRUCE LEHMAN

Attesting Officer

Commissioner of Patents and Trademarks